United States Patent
Bleckmann et al.

US006383503B1

(10) Patent No.: US 6,383,503 B1
(45) Date of Patent: May 7, 2002

(54) PREPARATIONS OF THE W/O EMULSION TYPE WITH AN INCREASED WATER CONTENT, ADDITIONALLY COMPRISING ONE OR MORE ALKYLMETHICONE COPOLYOLS AND/OR ALKYLDIMETHICONE COPOLYOLS, AND, IF DESIRED, CATIONIC POLYMERS

(75) Inventors: Andreas Bleckmann, Ahrensburg; Rainer Kropke, Schenefeld; Gunther Schneider, Hamburg; Stephanie Von Der Fecht, Schenefeld, all of (DE)

(73) Assignee: Beiersdorf AG, Hamburg (DE)

( * ) Notice: Subject to any disclaimer, the term of this patent is extended or adjusted under 35 U.S.C. 154(b) by 0 days.

(21) Appl. No.: 09/577,288

(22) Filed: May 23, 2000

(30) Foreign Application Priority Data

May 27, 1999 (DE) .......................................... 199 24 276

(51) Int. Cl.[7] .......................... A61K 7/00; A61K 7/021; A61K 7/48
(52) U.S. Cl. ................. 424/401; 424/78.03; 424/70.02; 424/70.12; 424/63; 424/69
(58) Field of Search .............................. 424/70.12, 401, 424/63, 78.03, 70.02, 69

(56) References Cited

U.S. PATENT DOCUMENTS 5,143,722 A * 9/1992 Hollenberg et al. ........... 424/63
5,470,551 A * 11/1995 Dubief et al. ............. 424/70.12
6,030,628 A * 2/2000 Schneider et al. .......... 424/401
6,162,423 A * 12/2000 Sebag et al. ............. 424/70.12

* cited by examiner

Primary Examiner—Diana Dudash
Assistant Examiner—Mina Haghighatian
(74) Attorney, Agent, or Firm—Norris McLaughlin & Marcus

(57) ABSTRACT

Water-in-oil emulsions (a) with a content of water and optionally water-soluble substances totalling at least 80% by weight, based on the total weight of the preparations, and with a content of lipids, emulsifiers and lipophilic constituents totalling at most 20% by weight, based in each case on the total weight of the preparations, (b) comprising at least one surface-active substance chosen from the group of alkylmethicone copolyols and/or alkyldimethicone copolyols, (c) comprising one or more lipid components which include the lipid phase of the emulsion, (d) where the weight ratio of (b) to (c) is chosen from the range 0.05 to 0.30, preferably 0.06 to 0.14, (e) if the water content is between 75 and 80% by weight, comprising one or more cationic polymers (f) if the water content is more than 80% by weight, not comprising a cationic polymer.

7 Claims, No Drawings

PREPARATIONS OF THE W/O EMULSION TYPE WITH AN INCREASED WATER CONTENT, ADDITIONALLY COMPRISING ONE OR MORE ALKYLMETHICONE COPOLYOLS AND/OR ALKYLDIMETHICONE COPOLYOLS, AND, IF DESIRED, CATIONIC POLYMERS

BACKGROUND OF THE INVENTION

The present invention relates to cosmetic and dermatological preparations, in particular those of the water-in-oil type, to processes for their preparation and to their use for cosmetic and medicinal purposes.

The human skin is man's largest organ and performs a number of vital functions. Having an average area of about 2 m² in adults, it has a prominent role as a protective and sensory organ. The purpose of this organ is to transmit and avert mechanical, thermal, actinic, chemical and biological stimuli. In addition, it has an important role as a regulatory and target organ in human metabolism.

The main aim of skin care in the cosmetics sense is to strengthen or rebuild the skin's natural function as a barrier against environmental influences (e.g. dirt, chemicals, microorganisms) and against the loss of endogenous substances (e.g. water, natural fats, electrolytes), and also to assist its horny layer in its natural regeneration ability where damage has occurred.

If the barrier properties of the skin are impaired, increased resorption of toxic or allergenic substances or infection by microorganisms may result, leading to toxic or allergic skin reactions.

Another aim of skin care is to compensate for the loss by the skin of sebum and water caused by daily washing. This is particularly important if the natural regeneration ability is inadequate. Furthermore, skin care products should protect against environmental influences, in particular against sun and wind, and delay skin ageing.

Medicinal topical compositions usually comprise one or more medicaments in an effective concentration. For the sake of simplicity, in order to clearly distinguish between cosmetic and medicinal use and corresponding products, reference is made to the legal provisions in the Federal Republic of Germany (e.g. Cosmetics Directive, Foods and Drugs Act).

Emulsions are generally taken to mean heterogeneous systems which consist of two liquids which are immiscible or miscible with one another only to a limited extent, which are usually referred to as phases. In an emulsion, one of the two liquids is dispersed in the form of very fine droplets in the other liquid.

If the two liquids are water and oil and oil droplets are very finely dispersed in water, this is an oil-in-water emulsion (O/W emulsion, e.g. milk). The basic character of an OIW emulsion is determined by the water. In the case of a water-in-oil emulsion (W/O emulsion, e.g. butter), the principle is reversed, the basic structure being determined here by the oil.

The person skilled in the art is of course aware of a large number of ways to formulate stable W/O preparations for cosmetic or dermatological use, for example in the form of creams and ointments which can be spread in the range from room temperature to skin temperature, or as lotions and milks, which are more likely flowable in this temperature range.

SUMMARY OF THE INVENTION

The object of the present invention was to provide preparations which can be formulated with a high or very high content of water-soluble and/or water-miscible substances, without impairing the galenical quality or other properties of the preparations.

According to K. J. Lissant: *The Geometry of High-Internal-Phase-Ratio Emulsions;* Journal of Colloid and Interface Science 22, 462–468 (1966), emulsions with an internal phase of >70% are defined as high internal phase emulsions. The preparation of stable, solid to semi-solid high internal phase water-in-oil emulsions, in particular those with a relatively high water content of 85% ("very high internal phase water-in-oil emulsions") and nevertheless with very good sensory properties is an unsolved problem. As a result of this very high water content in the emulsions, the latter "break" on the skin particularly rapidly (sensorily unpleasant) into their main constituents (hydrophilic and lipophilic components). Furthermore, the lipophilic components also separate into their individual constituents, meaning that the lipids "slide away" from one another on the skin (sensorily unpleasant).

The technique of varying the phase volume ratio (i.e. incorporating higher amounts of liquid lipids) which is usually used for water-in-oil emulsions can, because of the low lipid content, be used only to a limited extent in the case of high internal phase W/O emulsions, or not at all in the case of very high internal phase W/O emulsions.

DETAILED DESCRIPTION

Surprisingly, it has been found that water-in-oil emulsions (a) with a content of water and optionally water-soluble substances totalling at least 80% by weight, and with a content of lipids, emulsifiers and lipophilic constituents totalling at most 20% by weight, based in each case on the total weight of the preparations, (b) comprising at least one surface-active substance chosen from the group of alkylmethicone copolyols and/or alkyldimethicone copolyols, (c) comprising one or more lipid components which include the lipid phase of the emulsion, (d) where the weight ratio of (b) to (c) is chosen from the range 0.05 to 0.30, preferably 0.06 to 0.14, (e) if the water content is between 75 and 80% by weight, comprising one or more cationic polymers (f) if the water content is more than 80% by weight, not comprising a cationic polymer overcome the disadvantages of the prior art.

Surprisingly, the preparations according to the invention are extremely pleasant to use on the skin and are characterized by very high cosmetic elegance. Use of the compositions, which are familiar to persons skilled in the art without further inventive activity, makes it possible to achieve virtually any desired viscosities, meaning that the present invention can, for example, be formed as a flowable application form (for example a lotion) or as a semi-solid to solid preparation (for example as a cream).

One example of surface-active substances which are to be used particularly advantageously for the purposes of the present invention is cetyldimethicone copolyol, which is sold by Th. Goldschmidt AG under the trade name ABIL® EM 90.

Furthermore, the emulsifier laurylmethicone copolyol has been found to be particularly advantageous, which is obtainable under the trade name Dow Corning® 5200 Formulation Aid from Dow Corning Ltd.

The total amount of the surface-active substances used according to the invention in the finished cosmetic or dermatological preparations is advantageously chosen from the range 0.075–7.5% by weight, preferably 0.1–5.0% by weight, in particular 1.0–3.0% by weight, based on the total weight of the preparations.

The preparations according to the invention particularly advantageously comprise more than 85% by weight, in particular more than 88% by weight, of water and optionally water-soluble substances, based on the total weight of the preparations.

Surprisingly, it has in particular been found that the addition of from 0.01 to 10% (preferably 0.25–1.25%) of suitable cationic polymers makes it possible to prepare stable, solid to semisolid and/or flowable very high internal phase emulsions, which have excellent sensory properties.

Suitable cationic polymers are, for example, cationic cellulose derivatives (e.g. Polymer JR 400® from Amerchol), cationic starch, copolymers of diallyl-ammonium salts and acrylamides, quaternized vinypyrrolidone/vinylimidazole polymers (e.g. Luviquat® from BASF), condensation products of polyglycols and amines, quaternized collagen polypeptides (e.g. Lamequat® L from Grünau-Henkel), quaternized wheat polypeptides, polyethyleneimine, cationic silicone polymers, copolymers of adipic acid with dimethylaminohydroxypropyidiethylenetriamine, copolymers of acrylic acid with dimethyidiallyl-ammonium chloride (e.g. Merquate® 550 from Chemviron), polyaminopolyamides, cationic chitin derivatives, cationic guar gum (e.g. Jaguar® CBS from Hoechst Celanese), quaternized ammonium salt polymers (e.g. Mirapol® AD-1 from Miranol), and cationic biopolymers, such as, for example, chitosan (average molecular weight of from 50,000 to 2,000,000 g/mol [determined by means of gel permeation chromatography] and a degree of deacylation of from 10 to 99% [determined by means of $^1$H-NMR]).

For the purposes of the present disclosure, a general term for fats, oils, waxes and the like which is sometimes used is the term "lipids", with which the person skilled in the art is entirely familiar. The terms "oil phase" and "lipid phase" are also used synonymously.

The constituents of the lipid phase can advantageously be chosen from the group of polar and nonpolar lipid components, for example chosen from the group consisting of vaseline (petrolatum), paraffin oil and polyolefins. Of the polyolefins, polydecenes and hydrogenated polyisobutenes are the preferred substances.

For the purposes of the present invention, the oil phase can additionally advantageously comprise substances chosen from the group of esters of saturated and/or unsaturated, branched and/or unbranched alkanecarboxylic acids having a chain length of from 3 to 30 carbon atoms and saturated and/or unsaturated, branched and/or unbranched alcohols having a chain length of from 3 to 30 carbon atoms and from the group of esters of aromatic carboxylic acids and saturated and/or unsaturated, branched and/or unbranched alcohols having a chain length of from 3 to 30 carbon atoms. Such ester oils can then advantageously be chosen from the group consisting of isopropyl myristate, isopropyl palmitate, isopropyl stearate, isopropyl oleate, n-butyl stearate, n-hexyl laurate, n-decyl oleate, isooctyl stearate, isononyl stearate, isononyl isononanoate, 2-ethylhexyl palmitate, 2-ethylhexyl laurate, 2-hexyldecyl stearate, 2-octyldodecyl palmitate, oleyl oleate, oleyl erucate, erucyl oleate, erucyl erucate and also synthetic, semisynthetic and natural mixtures of such esters, such as, for example, jojoba oil.

The oil phase can also be chosen advantageously from the group of branched and unbranched hydrocarbons and hydrocarbon waxes, silicone oils, dialkyl ethers, the group of saturated or unsaturated, branched or unbranched alcohols, and fatty acid triglycerides, namely the triglycerol esters of saturated and/or unsaturated, branched and/or unbranched alkanecarboxylic acids having a chain length of from 8 to 24 carbon atoms, in particular 12–18 carbon atoms. The fatty acid triglycerides can, for example, be advantageously chosen from the group of synthetic, semisynthetic and natural oils, e.g. olive oil, sunflower oil, soya oil, peanut oil, rapeseed oil, almond oil, palm oil, coconut oil, palm kernel oil and the like.

Fatty and/or wax components which are to be used advantageously in the oil phase according to the invention can be chosen from the group of vegetable waxes, animal waxes, mineral waxes and petrochemical waxes. Examples which are favourable according to the invention are candelilla wax, carnauba wax, japan wax, esparto grass wax, cork wax, guaruma wax, rice germ oil wax, sugarcane wax, berry wax, ouricury wax, montan wax, jojoba wax, shea butter, beeswax, shellac wax, spermaceti, lanolin (wool wax), uropygial grease, ceresin, ozocerite (earth wax), paraffin waxes and microcrystalline waxes.

Other advantageous fatty and/or wax components are chemically modified waxes and synthetic waxes such as, for example, those obtainable under the trade names Syncrowax HRC (glyceryl tribehenate), Syncrowax HGLC ($C_{16-36}$-fatty acid triglyceride) and Syncrowax AW 1C ($C_{18-36}$-fatty acid) from CRODA GmbH, and also montan ester waxes, Sasol waxes, hydrogenated jojoba waxes, synthetic or modified beeswaxes (e.g. dimethicone copolyol beeswax and/or $C_{30-50}$-alkyl beeswax), polyalkylene waxes, polyethylene glycol waxes, but also chemically modified fats, such as, for example, hydrogenated vegetable oils (for example hydrogenated castor oil and/or hydrogenated coconut fatty glycerides), triglycerides, such as, for example, trihydroxystearin, fatty acids, fatty acid esters and glycol esters, such as, for example, $C_{20-40}$-alkyl stearate, $C_{20-40}$-alkylhydroxystearoyl stearate and/or glycol montanate. Also advantageous are certain organosilicon compounds, which have similar physical properties to the specified fatty and/or wax components, such as, for example, stearoxytrimethylsilane.

According to the invention, the fatty and/or wax components can be present either individually or as a mixture.

Any desired mixtures of such oil and wax components can also be used advantageously for the purposes of the present invention. In some instances, it can also be advantageous to use waxes, for example cetyl palmitate, as the lipid component of the oil phase.

Of the hydrocarbons, paraffin oil, hydrogenated polyolefins (e.g. hydrogenated polyisobutene), squalane and squalene can be used advantageously for the purposes of the present invention.

The oil phase can advantageously additionally have a content of cyclic or linear silicone oils or consist entirely of such oils, although it is preferable to use an additional content of other oil phase components apart from the silicone oil or the silicone oils.

Cyclomethicones (such as, for example, cyclotetrasiloxane and cyclopenta-siloxane) can also be used advantageously. However, other silicone oils can also be used advantageously for the purposes of the present invention, for example dimethicone (polydimethylsiloxanes of varying chain length such as, for example, Wacker AK 10, 20, 35, 50, 100), and polymethylphenylsiloxanes (such as, for example, phenyltrimethicones).

According to the invention, the oil phase can advantageously also comprise constituents chosen from the group of classical fats, i.e. essentially triglycerides.

The oils according to the invention are preferably chosen from the group of triglycerides of the following structure:

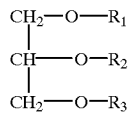

where $R_1$, $R_2$ and $R_3$ independently of one another are chosen from the group of branched and unbranched, alkylcarboxyl or alkenylcarboxyl groups having from 12 to 24 carbon atoms. In some instances, it is advantageous for one or more aliphatic hydrocarbon atoms of the alkylcarboxyl or alkenylcarboxyl groups to be substituted by hydroxyl groups.

It is particularly advantageous if $R_1$, $R_2$ and/or $R_3$ have from 16 to 20 carbon atoms and are chosen from the group of mono- to triunsaturated carboxylic acid radicals.

If $R_1$, $R_2$ and/or $R_3$ carry hydroxyl groups, the preferred alkenylcarboxyl radical is the ricinoleic acid radical.

It is also particularly advantageous to choose oils from the group consisting of soya oil, sunflower oil, wheat germ oil and castor oil.

The aqueous phase of the preparations according to the invention in some instances advantageously comprises alcohols, diols or polyols of low carbon number, and ethers thereof, preferably ethanol, isopropanol, propylene glycol, glycerol, ethylene glycol, ethylene glycol monoethyl ether or monobutyl ether, propylene glycol monomethyl, monoethyl or monobutyl ethers, diethylene glycol monomethyl or monoethyl ethers and analogous products, and also alcohols of low carbon number, e.g. ethanol, isopropanol, 1,2-propanediol, glycerol and, in particular, one or more thickeners which can advantageously be chosen from the group consisting of silicon dioxide, aluminium silicates, polysaccharides or derivatives thereof, e.g. hyaluronic acid, xanthan gum, hydroxypropylmethylcellulose, particularly advantageously from the group consisting of polyacrylates, preferably a polyacrylate from the group of carbopols, for example carbopol grades 980, 981, 1382, 2984, 5984, or also ETD (easy-to-disperse) grades 2001, 2020, 2050, in each case individually or in any combinations with one another.

A particular advantage of the present invention is that it permits high concentrations of polyols, in particular glycerol, to be used.

Particularly advantageous preparations are also obtained when antioxidants are used as additives or active ingredients. According to the invention, the preparations advantageously comprise one or more antioxidants. Antioxidants which are favourable but which are nevertheless optional may be all antioxidants which are customary or suitable for cosmetic and/or dermatological application.

The antioxidants are advantageously selected from the group consisting of amino acids (e.g. glycine, histidine, tyrosine, tryptophan) and their derivatives, imidazoles, (e.g. urocanic acid) and their derivatives, peptides, such as D,L-carnosine, D-carnosine, L-carnosine and their derivatives (e.g. anserine), carotenoids, carotenes (e.g. α-carotene, β-carotene, ω-lycopene) and their derivatives, lipoic acid and its derivatives (e.g. dihydrolipoic acid), aurothioglucose, propylthiouracil and other thiols (e.g. thioredoxin, glutathione, cysteine, cystine, cystamine and their glycosyl, N-acetyl, methyl, ethyl, propyl, amyl, butyl and lauryl, paimitoyl, oleyl, γ-linoleyl, cholesteryl and glyceryl esters) and their salts, dilauryl thiodipropionate, distearyl thiodipropionate, thiodipropionic acid and its derivatives (esters, ethers, peptides, lipids, nucleotides, nucleosides and salts) and sulphoximine compounds (e.g. buthionine sulphoximines, homocysteine sulphoximine, buthionine sulphones, penta-, hexa-, heptathionine sulphoximines) in very low tolerated doses (e.g. pmol to μmol/kg), and also (metal) chelating agents (e.g. α-hydroxy fatty acids, palmitic acid, phytic acid, lactoferrin), α-hydroxy acids (e.g. citric acid, lactic acid, malic acid), humic acid, bile acid, bile extracts, bilirubin, biliverdin, EDTA, EGTA and their derivatives, unsaturated fatty acids and their derivatives (e.g. γ-linolenic acid, linoleic acid, oleic acid), folic acid and its derivatives, ubiquinone and ubiquinol and their derivatives, vitamin C and derivatives (e.g. ascorbyl palmitate, Mg ascorbyl phosphate, ascorbyl acetate), tocopherols and derivatives (e.g. vitamin E acetate), vitamin A and derivatives (vitamin A palmitate) and coniferyl benzoate of benzoin resin, rutinic acid and its derivatives, ferulic acid and its derivatives, butylated hydroxytoluene, butylated hydroxyanisole, nordihydroguaiacic acid, nordihydroguaiareticic acid, trihydroxybutyrophenone, uric acid and its derivatives, mannose and its derivatives, zinc and its derivatives (e.g. ZnO, $ZnSO_4$), selenium and its derivatives (e.g. selenomethionine), stilbenes and their derivatives (e.g. stilbene oxide, trans-stilbene oxide), and the derivatives (salts, esters, ethers, sugars, nucleotides, nucleosides, peptides and lipids) of said active substances which are suitable according to the invention.

For the purposes of the present invention, oil-soluble antioxidants can be used particularly advantageously.

A surprising property of the present invention is that preparations according to the invention are very good vehicles for cosmetic or dermatological active ingredients into the skin, preferred active ingredients being antioxidants which are able to protect the skin against oxidative stress. Preferred antioxidants are vitamin E and its derivatives and vitamin A and its derivatives.

The amount of antioxidants (one or more compounds) in the preparations is preferably from 0.001 to 30% by weight, particularly preferably 0.05–20% by weight, in particular 1–10% by weight, based on the total weight of the preparation.

If vitamin E and/or its derivatives are used as the antioxidant or antioxidants, their respective concentrations are advantageously chosen from the range of 0.001–10% by weight, based on the total weight of the formulation.

If vitamin A or vitamin A derivatives or carotenes or their derivatives are used as the antioxidant or antioxidants, their respective concentrations are advantageously chosen from the range of 0.001–10% by weight, based on the total weight of the formulation.

The person skilled in the art is of course aware that cosmetic preparations are in most cases inconceivable without the customary auxiliaries and additives. The cosmetic and dermatological preparations according to the invention can, accordingly, also comprise cosmetic auxiliaries, as are customarily used in such preparations, for example bodying agents, stabilizers, fillers, preservatives, perfumes, antifoams, dyes, pigments which have a colouring action, thickeners, surface-active substances, emulsifiers, emollients, moisturizers and/or humectants, anti-inflammatory substances, additional active ingredients such as vitamins or proteins, sunscreens, insect repellants, bactericides, virucides, water, salts, antimicrobial, proteolytic or keratolytic substances, medicaments or other customary constituents of a cosmetic or dermatological formulation such as alcohols, polyols, polymers, foam stabilizers, organic solvents or also electrolytes.

The latter can be chosen, for example, from the group of salts containing the following anions: chlorides, also inorganic oxo element anions, of these, in particular sulphates, carbonates, phosphates, borates and aluminates. Electrolytes based on organic anions are also advantageous, e.g. lactates, acetates, benzoates, propionates, tartrates, citrates, amino acids, ethylenediaminetetraacetic acid and salts thereof and others. Preferred cations of the salts are ammonium, alkylammonium, alkali metal, alkaline earth metal, magnesium, iron or zinc ions. It does not need to be mentioned that only physiologically acceptable electrolytes should be used in cosmetics. Particular preference is given to potassium chloride, sodium chloride, magnesium sulphate, zinc sulphate and mixtures thereof.

Corresponding requirements apply mutatis mutandis to the formulation of medicinal preparations.

The W/O emulsions according to the invention can be used as a basis for cosmetic or dermatological formulations. The latter can have the customary composition and be used, for example, for the treatment and care of the skin and/or the hair, as lip care product, as deodorant product and as make-up or make-up remover product in decorative cosmetics or as a sunscreen preparation. For use, the cosmetic and dermatological preparations according to the invention are applied to the skin and/or the hair in a sufficient amount in a manner customary for cosmetics or dermatological compositions.

For the purposes of the present invention, cosmetic or topical dermatological compositions can accordingly, depending on their composition, be used, for example, as a skin protection cream, cleansing milk, sunscreen lotion, nourishing cream, day or night cream, etc. In some circumstances it is possible and advantageous to use the compositions according to the invention as a base for pharmaceutical formulations.

The low-viscosity cosmetic or dermatological compositions according to the invention can, for example, be in the form of preparations which can be sprayed from aerosol containers, squeezable bottles or by means of a pump device, or in the form of a liquid composition which can be applied by means of roll-on devices, but also in the form of an emulsion which can be applied from normal bottles and containers.

Suitable propellants for cosmetic or dermatological preparations which can be sprayed from aerosol containers for the purposes of the present invention are the customary known readily volatile, liquefied propellants, for example hydrocarbons (propane, butane, isobutane), which can be used alone or in a mixture with one another. Compressed air is also used advantageously.

The person skilled in the art is of course aware that there are propellants which are non-toxic per se which would be suitable in principle for realizing the present invention in the form of aerosol preparations, but which must nevertheless be avoided because of their unacceptable impact on the environment or other accompanying circumstances, in particular fluorinated hydrocarbons and chlorofluorocarbons (CFCs).

Cosmetic and dermatological preparations which are in the form of a sunscreen are also favourable. As well as the active ingredient combinations according to the invention, these preferably additionally comprise at least one UV-A filter substance and/or at least one UV-B filter substance and/or at least one inorganic pigment.

For the purposes of the present invention, however, it is also advantageous to provide cosmetic and dermatological preparations whose main purpose is not protection against sunlight, but which nevertheless have a content of UV protectants. Thus, for example, UV-A or UV-B filter substances are usually incorporated into day creams.

UV protectants, like antioxidants and, if desired, preservatives, also effectively protect the preparations themselves against decay.

Preparations according to the invention can advantageously comprise further substances which absorb UV radiation in the UV-B range, the total amount of filter substances being, for example, from 0.1% by weight to 30% by weight, preferably from 0.5 to 10% by weight, in particular from 1.0 to 6.0% by weight, based on the total weight of the preparations, in order to provide cosmetic preparations which protect the hair and/or the skin from the whole region of ultraviolet radiation. They can also be used as sunscreens for the hair or the skin.

If the emulsions according to the invention contain UV-B filter substances, the latter may be oil-soluble or water-soluble. Examples of oil-soluble UV-B filters which are advantageous according to the invention are:

3-benzylidenecamphor derivatives, preferably 3-(4-methylbenzylidene)camphor, 3-benzylidenecamphor;

4-aminobenzoic acid derivatives, preferably 2-ethylhexyl 4-(dimethylamino)benzoate, amyl 4-(dimethylamino)benzoate;

esters of cinnamic acid, preferably 2-ethylhexyl 4-methoxycinnamate, isopentyl 4-methoxycinnamate;

esters of salicylic acid, preferably 2-ethylhexyl salicylate, 4-isopropylbenzyl salicylate, homomenthyl salicylate;

derivatives of benzophenone, preferably 2-hydroxy-4-methoxybenzophenone, 2-hydroxy-4-methoxy-4'-methylbenzophenone, 2,2'-dihydroxy-4-methoxybenzophenone;

esters of benzalmalonic acid, preferably di(2-ethylhexyl) 4-methoxybenzalmalonate;

derivatives of 1,3,5-triazine, preferably 2,4,6-trianilino(p-carbo-2'-ethyl-1'-hexyloxy)-1,3,5-triazine.

The list of said UV-B filters, which may be used in combination with the active ingredient combinations according to the invention is of course not intended to be limiting.

It can also be advantageous to formulate lipodispersions according to the invention with UV-A filters which have hitherto been customarily present in cosmetic preparations. These substances are preferably derivatives of dibenzoylmethane, in particular 1-(4'-tert-butylphenyl)-3-(4'-methoxyphenyl)propane-1,3-dione and 1-phenyl-3-(4'-isopropylphenyl)propane-1,3-dione.

Cosmetic and dermatological preparations according to the invention can also comprise inorganic pigments which are customarily used in cosmetics for protecting the skin against UV rays. These are oxides of titanium, zinc, iron, zirconium, silicon, manganese, aluminium, cerium and mixtures thereof, and modifications in which the oxides are the active agents. Particular preference is given to pigments based on titanium dioxide.

Further constituents which can be used are:

fats, waxes and other natural and synthetic fatty substances, preferably esters of fatty acids with alcohols of low carbon number, e.g. with isopropanol, propylene glycol or glycerol, or esters of fatty alcohols with alkanoic acids of low carbon number or with fatty acids;

alcohols, diols or polyols of low carbon number, and their ethers, preferably ethanol, isopropanol, propylene glycol, glycerol, ethylene glycol, ethylene glycol monoethyl or monobutyl ethers, propylene glycol monomethyl, monoethyl or monobutyl ethers, diethylene glycol monomethyl or monoethyl ethers and analogous products.

Preparations according to the invention can also comprise active ingredients (one or more compounds) which are chosen from the group: acetylsalicylic acid, atropine, azulene, hydrocortisone and derivatives thereof, e.g. hydrocortisone-17 valerate, vitamins, e.g. ascorbic acid and derivatives thereof, vitamins of the B and D series, very favourably vitamin $B_1$, vitamin $B_{12}$ and vitamin $D_1$, but also bisabolol, unsaturated fatty acids, namely the essential fatty acids (often also called vitamin F), in particular γ-linolenic acid, oleic acid, eicosapentanoic acid, docosahexanoic acid and derivatives thereof, chloramphenicol, caffeine, prostaglandins, thymol, camphor, extracts or other products of a vegetable and animal origin, e.g. evening primrose oil, star flower oil or currant seed oil, fish oils, cod-liver oil or also ceramides or ceramide-like compounds etc. It is also advantageous to choose the active ingredients from the group of refatting substances, for example purcellin oil, Eucerit® and Neocerit®.

The amount of such active ingredients (one or more compounds) in the preparations according to the invention is preferably from 0.001 to 30% by weight, particularly preferably 0.05–20% by weight, in particular 1–10% by weight, based on the total weight of the preparation.

The examples below serve to illustrate the present invention without limiting it. The numerical values in the examples refer to percentages by weight, based on the total weight of the respective preparations.

EXAMPLE 1 (W/O CREAM)

| | % by weight |
|---|---|
| Cetyldimethicone copolyol | 1.50 |
| Caprylic acid/capric acid triglycerides | 4.00 |
| Dicaprylyl ether | 3.00 |
| Octyldodecanol | 3.00 |
| Glycerol | 3.00 |
| Sodium chloride | 0.70 |
| Perfume, preservatives, dyes | q.s. |
| Water | ad100.00 |

EXAMPLE 2 (W/O CREAM)

| | % by weight |
|---|---|
| Laurylmethicone copolyol | 2.00 |
| Octyldodecanol | 3.00 |
| $C_{12-15}$-alkyl benzoates | 3.00 |
| Squalane | 3.00 |
| Paraffinum liquidum | 8.00 |
| Glycerol | 3.00 |
| Sodium chloride | 0.70 |
| Perfume, preservatives, dyes | q.s. |
| Water | ad100.00 |

EXAMPLE 3 (W/O CREAM)

| | % by weight |
|---|---|
| Cetyldimethicone copolyol | 2.00 |
| Squalane | 2.00 |
| Paraffinum liquidum | 3.00 |
| Stearyl heptanoate | 1.00 |
| Hydrogenated polyisobutene | 3.00 |
| Glycerol | 3.00 |
| Sodium chloride | 0.70 |
| Perfume, preservatives, dyes | q.s. |
| Water | ad100.00 |

EXAMPLE 4 (W/O CREAM)

| | % by weight |
|---|---|
| Cetyldimethicone copolyol | 1.50 |
| Paraffinum liquidum | 16.50 |
| Tocopherol acetate | 0.50 |
| Glycerol | 3.00 |
| Panthenol | 0.30 |
| 1,3-Butylene glycol | 1.00 |
| Serine | 0.30 |
| Biotin | 0.10 |
| Distarch phosphate | 1.00 |
| Sodium chloride | 0.70 |
| Perfume, preservatives, dyes | q.s. |
| Water | ad100.00 |

EXAMPLE 5 (W/O CREAM)

| | % by weight |
|---|---|
| Cetyldimethicone copolyol | 2.00 |
| Isohexadecane | 2.00 |
| Paraffinum liquidum | 2.00 |
| Butylmethoxydibenzoylmethane | 1.00 |
| Octyl methoxycinnamate | 2.00 |
| Methylbenzylidenecamphor | 1.50 |
| Octyltriazone | 0.50 |
| Titanium dioxide | 1.00 |
| Zinc oxide | 1.00 |
| Glycerol | 1.00 |
| Sodium chloride | 0.70 |
| Perfume, preservatives, dyes | q.s. |
| Water | ad100.00 |

EXAMPLE 6 (W/O CREAM)

| | % by weight |
|---|---|
| Laurylmethicone copolyol | 1.50 |
| Isohexadecane | 4.50 |
| Paraffinum subliquidum | 17.50 |
| Glycerol | 3.00 |
| Sodium chloride | 0.70 |
| Chitosan | 0.40 |
| Lactic acid (90% strength) | 0.30 |
| Perfume, preservatives, dyes | q.s. |
| Water | ad100.00 |

EXAMPLE 7 (W/O CREAM)

|  | % by weight |
| --- | --- |
| Cetyldimethicone copolyol | 2.50 |
| Caprylic acid/capric acid triglycerides | 6.00 |
| Dicaprylyl ether | 7.50 |
| Octyldodecanol | 7.50 |
| Glycerol | 30.00 |
| Propylene glycol | 5.00 |
| Magnesium sulphate | 0.70 |
| Polyquaternium-10 | 1.00 |
| Perfume, preservatives, dyes | q.s. |
| Water | ad 100.00 |

EXAMPLE 8 (WATER-IN-SILICONE CREAM)

|  | % by weight |
| --- | --- |
| Laurylmethicone copolyol | 1.50 |
| Cetyldimethicone copolyol | 0.50 |
| Cyclomethicone | 17.00 |
| Sorbitol | 15.00 |
| Sodium chloride | 0.70 |
| Perfume, preservatives, dyes | q.s. |
| Water | ad 100.00 |

EXAMPLE 9 (WATER-IN-SILICONE CREAM)

|  | % by weight |
| --- | --- |
| Cetyldimethicone copolyol | 1.50 |
| Laurylmethicone copolyol | 0.50 |
| Cyclomethicone | 18.00 |
| Dimethicone | 4.00 |
| Glycerol | 5.00 |
| Magnesium sulphate | 0.70 |
| Polyquaternium-10 | 1.00 |
| Perfume, preservatives, dyes | q.s. |
| Water | ad 100.00 |

EXAMPLE 10 (W/O CREAM)

|  | % by weight |
| --- | --- |
| Laurylmethicone copolyol | 1.00 |
| Cetyldimethicone copolyol | 1.00 |
| Sunflower oil | 3.00 |
| Dicaprylyl ether | 3.00 |
| Paraffinum liquidum | 4.00 |
| Glycerol | 3.00 |
| Sodium chloride | 0.70 |
| Perfume, preservatives, dyes | q.s. |
| Water | ad 100.00 |

EXAMPLE 11 (W/O CREAM)

|  | % by weight |
| --- | --- |
| Cetyldimethicone copolyol | 1.50 |
| Caprylic acid/capric acid triglycerides | 5.00 |
| Jojoba oil | 2.00 |
| Dimethicone | 2.00 |
| Dimethiconol | 0.50 |
| Cyclomethicone | 3.00 |
| Dimethicone copolyol | 0.20 |
| Distarch phosphate | 1.00 |
| Glycerol | 3.00 |
| Sodium chloride | 0.70 |
| Perfume, preservatives, dyes | q.s. |
| Water | ad 100.00 |

EXAMPLE 12 (EMULSION MAKE-UP)

|  | % by weight |
| --- | --- |
| Cetyldimethicone copolyol | 1.50 |
| Octyldodecanol | 2.00 |
| $C_{12-15}$-alkyl benzoates | 2.00 |
| Squalane | 3.00 |
| Paraffinum liquidum | 3.00 |
| Distarch phosphate | 0.50 |
| Dimethicone | 0.50 |
| Glycerol | 1.50 |
| Magnesium silicate | 1.00 |
| Mica | 0.50 |
| Iron oxides | 0.50 |
| Titanium dioxide | 1.00 |
| Talc | 1.00 |
| Tapioca starch | 0.25 |
| Perfume, preservatives, dyes | q.s. |
| Water | ad 100.00 |

General Remarks Regarding the Example Formulations

1) Adjust pH of the aqueous phase of the emulsion by adding acids which form water-soluble salts with chitosan (such as, for example, lactic acid, glycolic acid, acetic acid, salicylic acid, aspartic acid) to ph of water phase of <6.0 (preferably from 3.5 to 5.5).
2) Chitosan: average molecular weight of from 50,000 to 2,000,000 g/mol [determined by means of gel permeation chromatography] and a degree of deacylation of from 10 to 99% [determined by means of $^1$H-NMR].

What is claimed is:

1. Water-in-oil emulsions
   (a) with a content of water and optionally water-soluble substances totalling at least 80% by weight, based on the total weight of the preparations, and with a content of lipids, emulsifiers and lipophilic constituents totalling at most 20% by weight, based in each case on the total weight of the preparations,
   (b) comprising at least one surface-active substance selected from the group consisting of alkylmethicone copolyols, alkyldimethicone copolyols, and combinations thereof
   (c) comprising one or more lipid components which include the lipid phase of the emulsion,
   (d) where the weight ratio of (b) to (c) is chosen from the range 0.05 to 0.30,
   (e) if the water content is between 75 and 80% by weight, comprising one or more cationic polymers
   (f) if the water content is more than 80% by weight, not comprising a cationic polymer.

2. Emulsions according to claim 1, characterized in that the surface-active substance chosen is cetyldimethicone copolyol.

3. Emulsions according to claim 1, characterized in that the surface-active substance chosen is laurylmethicone copolyol.

4. Emulsions according to claim 1, wherein the total amount of said alkylmethicone copolyols, alkyldimethicone copolyols or combinations thereof is chosen from the range 0.075–7.5% by weight, based on the total weight of the preparations.

5. Emulsions according to claim 1, characterized in that they comprise more than 85% by weight, in particular more than 88% by weight, of water and water-soluble substances, based on the total weight of the preparations.

6. Emulsions according to claim 1, characterized in that they comprise from 0.01 to 10%, preferably 0.25–1.25%, of cationic polymers.

7. Emulsions according to claim 1, wherein the cationic polymer is selected from the group consisting of cationic cellulose derivatives, cationic starch, copolymers of diallylammonium salts and acrylamides, quaternized vinylpyrrolidone/vinylimidazole polymers, condensation products of polyglycols and amines, quaternized collagen polypeptides, quaternized wheat polypeptides, polyethyleneimine, cationic silicone polymers, copolymers of adipic acid with dimethylaminohydroxypropyidiethylenetriamine, copolymers of acrylic acid with dimethyldiallylammonium chloride, polyaminopolyamides, cationic chitin derivatives, cationic guar gum, quaternized ammonium salt polymers, cationic biopolymers, and combinations thereof.

* * * * *